United States Patent
Wu

(10) Patent No.: US 10,932,685 B2
(45) Date of Patent: Mar. 2, 2021

(54) CATHETER WITH SUPPORTING STRUCTURE HAVING VARIABLE DIMENSIONS

(71) Applicant: Biosense Webster (Israel) Ltd., Yokneam (IL)

(72) Inventor: Steven Wu, San Jose, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 313 days.

(21) Appl. No.: 15/401,166

(22) Filed: Jan. 9, 2017

(65) Prior Publication Data
US 2018/0193089 A1    Jul. 12, 2018

(51) Int. Cl.
| | | |
|---|---|---|
| *A61B 5/042* | (2006.01) | |
| *A61B 18/14* | (2006.01) | |
| *A61B 5/00* | (2006.01) | |
| *A61M 25/00* | (2006.01) | |
| *A61B 34/20* | (2016.01) | |
| *A61B 18/00* | (2006.01) | |

(52) U.S. Cl.
CPC .......... *A61B 5/0422* (2013.01); *A61B 5/6858* (2013.01); *A61B 5/6859* (2013.01); *A61B 18/1477* (2013.01); *A61B 18/1492* (2013.01); *A61M 25/001* (2013.01); *A61B 2018/0016* (2013.01); *A61B 2018/00214* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2018/1405* (2013.01); *A61B 2018/1467* (2013.01); *A61B 2034/2065* (2016.02)

(58) Field of Classification Search
CPC .................................................... A61B 5/0422
See application file for complete search history.

(56) References Cited

U.S. PATENT DOCUMENTS

| | | | |
|---|---|---|---|
| 5,391,199 | A | 2/1995 | Ben-Haim |
| 5,465,717 | A * | 11/1995 | Imran ................. A61B 5/0422 600/374 |
| 5,772,590 | A | 6/1998 | Webster, Jr. |
| 6,064,905 | A | 5/2000 | Webster, Jr. et al. |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,748,255 | B2 | 6/2004 | Fuimaono et al. |
| 6,973,340 | B2 | 12/2005 | Fuimaono et al. |

(Continued)

FOREIGN PATENT DOCUMENTS

WO    96/05768    2/1996

*Primary Examiner* — Lee S Cohen
(74) *Attorney, Agent, or Firm* — Dergosits & Noah LLP; Todd A. Noah

(57) ABSTRACT

This disclosure is directed to a catheter having a multi-electrode assembly with a high electrode density. The multi-electrode assembly may be a basket-shaped electrode assembly or a brush-shaped electrode assembly each having a plurality of spines. Each spine includes a flexible wire core of a shape memory material. The flexible wires may have variable cross-section s to control the movement and stiffness of the spines.

6 Claims, 4 Drawing Sheets

(56) References Cited

U.S. PATENT DOCUMENTS

| | | | |
|---|---|---|---|
| 8,346,339 B2* | 1/2013 | Kordis | A61B 5/0422 600/374 |
| 8,588,885 B2* | 11/2013 | Hall | A61B 5/0422 600/374 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2016/0183877 A1* | 6/2016 | Williams | A61B 18/1492 600/374 |

* cited by examiner

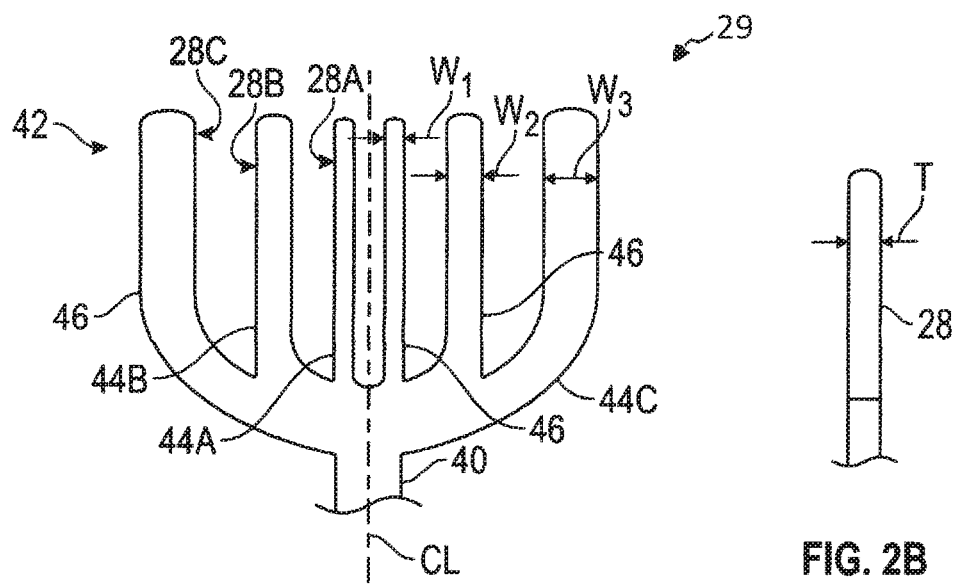
FIG. 2A
FIG. 2B
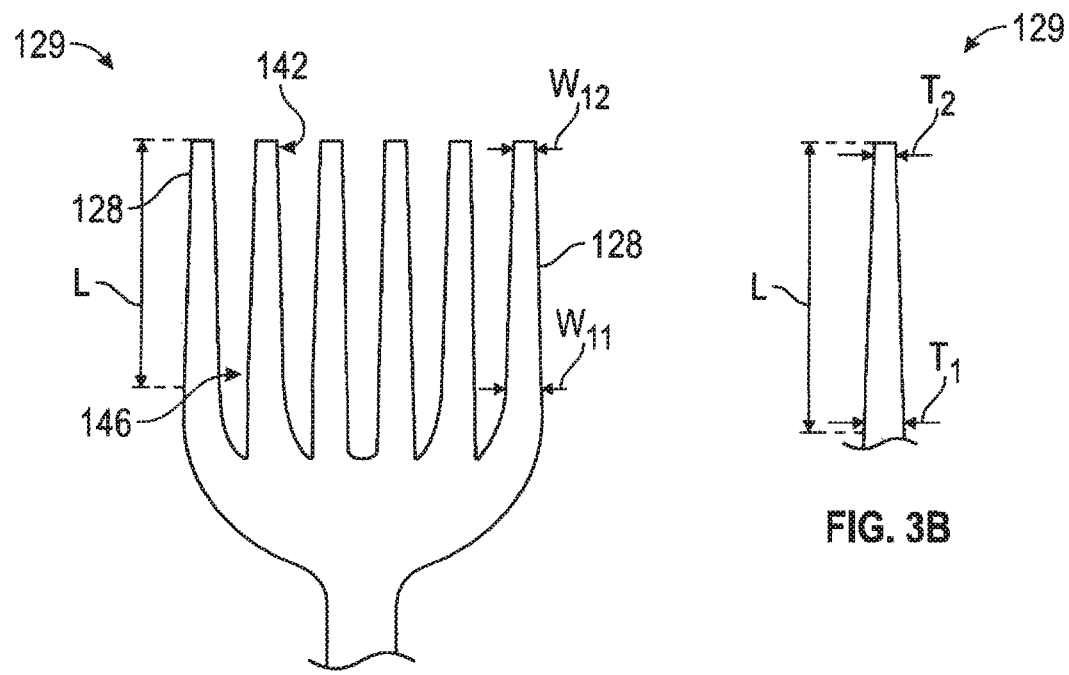
FIG. 3A
FIG. 3B

CATHETER WITH SUPPORTING STRUCTURE HAVING VARIABLE DIMENSIONS

FIELD OF THE PRESENT DISCLOSURE

This invention relates to electrophysiologic (EP) catheters, in particular, EP catheters for mapping and/or ablation in the heart. More particularly, the invention relates to EP catheters having support structure with variable dimensions.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that an multi-electrode assembly be capable of detecting in as few beats as possible, including a single beat, as much of the electrical function of the region in which the electrode assembly is deployed, such as the left or right atrium as possible. By implementing a greater number of electrodes in the electrode assembly, correspondingly greater and more complete coverage of the region may be obtained. Further, the increased number of electrodes may reduce or eliminate the need to reposition the electrode assembly to access all of the desired area in the region. Often, increasing the number of electrodes corresponds with an increase in the number of spines or other structures that support the electrodes. One problem with prior art designs with multiple spines is that the movement of the spines when deployed is not easily controlled and may lead to the spines moving closer together so that the spines and electrodes may be touching or overlapping. Touching or overlapping spines and electrodes may lead to inaccurate data collection or inefficient treatment of the tissue. Another issue with prior devices is that the spines may not be robust enough to maintain contact with the tissue to be mapped or treated. As such, there is a need for a multi-electrode assembly having an improved support member for controlling the movement of the spines and maintaining electrode contact with the tissue. The techniques of this disclosure satisfy this and other needs as described in the following materials.

SUMMARY

The present disclosure is directed to a catheter including an elongated catheter body extending along a longitudinal axis, the elongated catheter body having a proximal end and a distal end, a flexible wire assembly positioned at the distal end of the elongated catheter body formed from a shape memory material, the flexible wire assembly having a plurality of flexible wires, each flexible wire having a proximal end and a distal end and wherein at least one of the flexible wires has a variable cross-section. The catheter further includes a plurality of spines formed from the plurality of flexible wires and a plurality of electrodes and cabling attached to each spine.

In one aspect, the distal ends of the plurality of flexible wires are joined at a distal hub to form a basket-shapes multi-electrode device.

In one aspect, the at least one flexible wire has a variable thickness where a middle portion of the flexible wire has a first thickness and a proximal portion of the flexible wire has a second thickness, where the second thickness is greater than the first thickness, and where the at least one flexible wire has a distal portion with a third thickness, where the third thickness is greater than the first thickness.

In one aspect, the second thickness is equal to the third thickness, wherein the thickness of the flexible wire tapers from the distal portion to the middle portion; and wherein the thickness of the flexible wire tapers from the proximal portion to the middle portion.

In one aspect, the at least one flexible wire has a width that is constant from the proximal portion to the distal portion.

In one aspect, the at least one flexible wire has a width that tapers from the proximal portion to the middle portion, and wherein the width tapers from the distal portion to the middle portion.

In one aspect, the flexible wire assembly comprises a brush-shaped flexible wire assembly, wherein the distal end of each flexible wire is unattached to an adjacent flexible wire.

In one aspect, the plurality of flexible wires comprises at least one flexible wire with a first width and at least one flexible wire with a second width, wherein the second width is greater than the first width.

In one aspect, the plurality of flexible wires comprises at least one flexible wire with a third width, wherein the third width is greater than the second width.

In one aspect, the plurality of flexible wires comprises at least one flexible wire with a thickness, wherein the thickness is a constant thickness along a length of the flexible wires.

In one aspect, the plurality of the flexible wires comprises at least one flexible wire with a variable thickness, wherein the variable thickness tapers from a first thickness at the proximal portion of the flexible wire to a second thickness at the distal portion of the flexible wire.

In one aspect, the plurality of flexible wires comprise a proximal portion with a first width and a distal portion with a second width; wherein the first width is greater than the second width; and wherein the width tapers along a length of the plurality of flexible wires from the proximal portion having the first width to the distal portion having the second width.

In one aspect, the plurality of flexible wires comprise a proximal portion with a first thickness and a distal portion with a second thickness; wherein the first thickness is greater than the second thickness; and wherein the thickness tapers along a length of the plurality of flexible wires from the proximal portion having the first thickness to the distal portion having the second thickness.

In one aspect, the shape memory material comprises a nickel titanium alloy.

The present disclosure is also directed to a method for forming a catheter including forming an elongate catheter body, forming a flexible wire assembly from a shape memory material, the flexible wire assembly having a plurality of flexible wires, wherein the plurality of flexible wires has a variable cross-section, heating the flexible wire assembly to heat set the flexible wire assembly, connecting a plurality of electrodes and cabling to each of the plurality of flexible wires to form a multi-electrode assembly and connecting the multi-electrode assembly to a distal end of the elongate catheter body.

In one aspect, the multi-electrode assembly is a brush-shaped electrode assembly.

In one aspect, the plurality of flexible wires has a first width at a proximal portion and a second width at a distal portion, wherein the width tapers from the first width at the proximal portion toward the second width at the distal portion.

In one aspect, the plurality of flexible wires has at least one flexible wire with a first width, and at least one flexible wire with a second width; wherein the second width is greater than the first width.

In one aspect, the plurality of flexible wires has at least one flexible wire with a third width, the third width greater than the second width.

BRIEF DESCRIPTION OF THE DRAWINGS

Further features and advantages will become apparent from the following and more particular description of the preferred embodiments of the disclosure, as illustrated in the accompanying drawings, which are not drawn to scale, and in which like referenced characters generally refer to the same parts or elements throughout the views, and in which:

FIGS. 2A and 2B are schematic views of a brush-shaped flexible wire assembly, according to one embodiment.

FIGS. 3A and 3B are schematic views of another flexible wire assembly, according to one embodiment.

DETAILED DESCRIPTION

Figure 1:
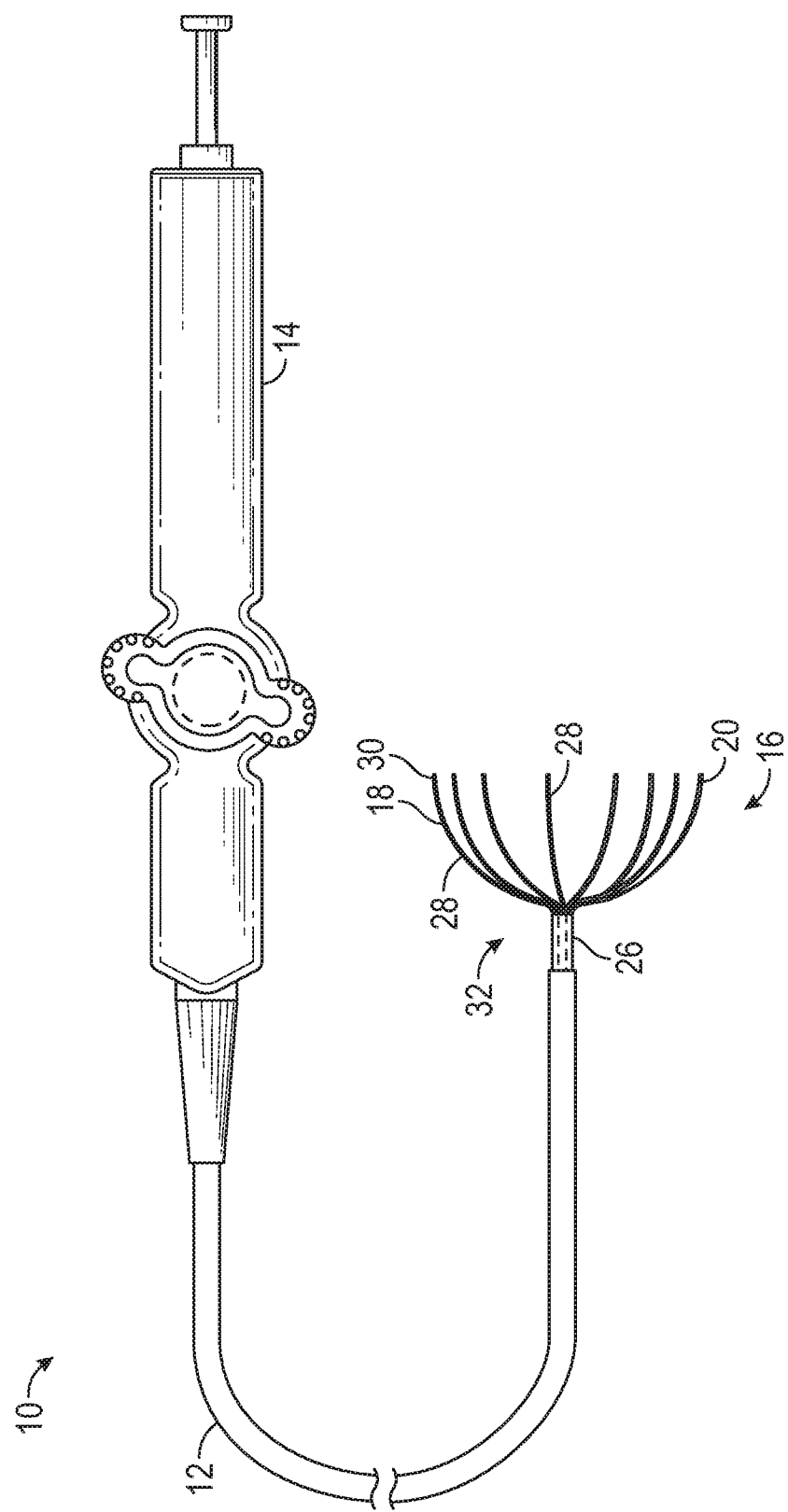
FIG. 1 is a schematic view of a catheter of the present invention, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

Multi-electrode assemblies are often used within the heart chamber to analyze or map the electrical activity. It is desirable to collect this data as quickly as possible to decrease the procedure time as well as to limit the stress on the patient. Medical devices with multiple electrodes distributed amongst multiple spines have been developed to shorten this procedure time. The increase in the number of spines to accommodate the electrodes has created an opportunity to better control the placement and relative stiffness of the spines as they are deployed and used at the treatment site. According to the techniques of this disclosure, the spines of a basket-shaped or brush-shaped multi-electrode assembly are configured to have differing dimensions along the spinal support to control the movement of the spines and to maintain electrode contact with the tissue during the procedure.

Referring now to FIG. 1, catheter 10 comprises an elongated catheter body 12 having proximal and distal ends and a control handle 14 at the proximal end of the catheter body. Catheter 10 further comprises an electrode assembly 16 at the distal end of catheter body 12. Electrode assembly 16 is a multi-electrode assembly comprising a plurality of spines. In one embodiment, as shown in FIG. 1, electrode assembly 16 is a brush-shaped electrode assembly 16 having a plurality of spines 18, each carrying multiple electrodes 20, and mounted at the distal end of the catheter body 12. In another embodiment, as discussed below and shown in FIG. 4, electrode assembly 16 comprises a basket-shaped electrode assembly. Catheter body 12 comprises an elongated tubular construction having a single, axial or central lumen 26, but can optionally have multiple lumens if desired. To enable accurate mapping of electrical signals, it may be desirable to provide an array of electrodes with a relatively high density. As such, the number of spines 18 employed may vary from four to sixteen, or any other suitable number. The distal ends of spines 18 are separated from adjacent spines. Each spine 18 may include multiple electrodes 20, such as at least six and up to approximately 16 electrodes per spine, or any other number of electrodes to suit a particular application. Similarly, the electrodes may be evenly distributed along the spine or may be skewed proximally, centrally or distally to facilitate analysis of the measured electrical signals.

Catheter body 12 is flexible, i.e., bendable, but substantially non-compressible along its length. Catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. In one aspect, the overall diameter of the catheter body 12 may relate to the number of electrodes 20 implemented by electrode assembly 16 in order to accommodate the associated electrical leads. For example, a twelve-spine design with each spine carrying sixteen electrodes for a total of 192 electrodes, a ten-spine design with each spine carrying sixteen electrodes for a total of 160 electrodes and an eight-spine design with each spine carrying sixteen electrodes for a total of 128 electrodes may utilize up to a 10.0 french catheter body. Likewise the thickness of the outer wall is not critical, but may be thin enough so that the central lumen can accommodate lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Spines 18 include a shape memory material, as described below, that facilitates assuming an expanded arrangement. When the brush-shaped electrode assembly 16 is deployed, it assumes an expanded configuration whereby the spines 18 expand in a generally planar fashion and into contact with the walls of the chamber in which it has been deployed, such as the left atrium.

In one aspect, an electrophysiologist may introduce a guiding sheath, guidewire and dilator into the patient, as is generally known in the art. As an example, a suitable guiding sheath for use in connection with the inventive catheter is a 10 french DiRex™ Guiding Sheath (commercially available from BARD, Murray Hill, N.J.). The guidewire is inserted, the dilator is removed, and the catheter is introduced through the guiding sheath whereby the guidewire lumen 26 permits the catheter to pass over the guidewire. In one exemplary procedure, the catheter is first introduced to the right atrium (RA) via the inferior vena cava (IVC), where it passes through the septum (S) in order to reach the left atrium (LA).

As will be appreciated, the guiding sheath 24 covers the spines 18 of the multi-electrode assembly 16 in a collapsed delivery position so that the entire catheter can be passed through the patient's vasculature to the desired location. Once the distal end of the catheter reaches the desired location, e.g., the left atrium, the guiding sheath is withdrawn to expose the multi-electrode assembly 16. Upon withdrawal of the guiding sheath, the shape memory material of the multi-electrode assembly expands the device within the chamber. With the electrode assembly 16 expanded, the ring electrodes 20 contact atrial tissue. As recognized by one skilled in the art, the electrode assembly 16 may be fully or partially expanded, straight or deflected, in a variety of configurations depending on the configuration of the region of the heart being mapped or treated.

When the electrode assembly 16 is expanded, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the catheter with the multiple electrodes on the brush-shaped electrode assembly, the electrophysiologist can map the selected region of the heart. The embodiment described above utilized a plurality of ring electrodes. In another embodiment, the multi-electrode assembly uses a plurality of printed circuit board (PCB) electrodes. In this embodiment, the PCB electrodes may be positioned on any portion of the spines that may contact the tissue to be treated. For example, the PCB electrode may be on a first side, a second side or both the first and second side of the spine. The location of the PCB may be dependent on the application of the particular device.

The brush-shaped electrode assembly 16, as shown in FIG. 1, features a total of eight spines 18, each carrying ten electrodes 20. In other embodiments, different numbers of spines 18 and/or electrodes 20 may be employed, each of which may be evenly or unevenly distributed as desired. The proximal ends of the spines 18 may be secured to the distal end 32 of the catheter body 12. Lumen 26 may be used as a guidewire lumen. In some embodiments, lumen 26 may also be used to supply a suitable irrigation fluid, such as heparinized saline, to the electrode assembly 16. A fitting (not shown) in the control handle 14 may be provided to conduct irrigation fluid from a suitable source or pump into the lumen 26.

Each spine 18 may include cabling with built-in or embedded lead wires for the electrodes 20 carried by the spine. The cabling has a core, and a plurality of generally similar wires each covered by an insulating layer that enables each wire to be formed and to function as a conductor. The core provides a lumen in which can pass other components such as a support structure in the form of flexible wire 28, discussed in further detail below, and/or additional lead wire(s), cables, tubing or other components. Cabling suitable for use with the present invention is described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which have been incorporated above. Each cabling (with embedded lead wires) may extend to the control handle 14 for suitable electrical connection of wires, thereby allowing signals measured by electrodes 20 to be detected.

Each spine 18 may comprise a flexible wire 28 support with a non-conductive covering 30 on which one or more of the ring electrodes 20 are mounted. Each ring electrode 20 may be configured as monopolar or bipolar, as known in the art. In an embodiment, the flexible wires 28 may be formed from a shape memory material to facilitate the transition between expanded (deployed) and collapsed (delivery) configurations and the non-conductive coverings 30 may each comprise biocompatible plastic tubing, such as polyurethane or polyimide tubing. A plurality of flexible wires 28 may be joined to form a flexible wire assembly. The embodiments of the flexible wire assembly 29, illustrated below in FIGS. 2A to 5B, provide an improvement to the control and stability of the multi-electrode device as the spines contact the tissue to be mapped and/or treated.

FIGS. 2A and 2B illustrate one embodiment of an improved flexible wire assembly 29. Flexible wire assembly 29 comprises a plurality of flexible wires 28. In one embodiment, flexible wire assembly 29 is composed of nitinol, a nickel-titanium alloy. In one embodiment, flexible wire assembly 29 is manufactured from a single sheet of nitinol alloy. In another embodiment, flexible wire assembly 29 is manufactured from a single tube of nitinol alloy and formed into the brush shape. The nitinol alloy may be laser cut and/or drilled to form the brush-shaped pattern. In yet other embodiments, individual flexible wires 28 are manufactured and then joined together at their proximal ends to form the flexible wire assembly. In each of these embodiments, the proximal ends of the flexible wires 28 are joined to a distal end 32 of catheter 12.

As mentioned above, the flexible wire assembly 29 is composed of nitinol alloy, a shape memory material. During manufacture, the flexible wire assembly is heat set into a "memorized" shape, which is also referred to as the deployed shape or deployed configuration. At body temperature, nitinol wire is flexible and elastic and, like most shape memory metals, nitinol wires deform when subjected to minimal force and return to their shape in the absence of that force. During manufacture, the nitinol material is heated and formed into the desired shape. This shape is then heat set, as is known in the art. The brush-shaped electrode assembly 16 will have a three dimensional shape that can be collapsed (deformed) to be placed into a guiding sheath and then returned to its expanded shape memory configuration upon delivery to the desired region of the patient upon release from the guiding sheath. One of ordinary skill in the art will recognize that other shape memory materials may be used in place of the nitinol alloy, for example, other shape memory metals and shape memory polymers.

As mentioned above in describing FIG. 1, the flexible wire assembly 29 provides a supporting structure for the spines 18 and the electrodes 20 carried on those spines. However, to improve the function of multi-electrode devices over that of the prior art, the inventor has determined that varying the dimensions and shape of the cross sections of the flexible wire assembly will offer better tissue contact and control of the spines carrying the electrodes. FIG. 2A illustrates a flexible wire assembly having flexible wires 28 that have different widths. In this embodiment, the width W of the flexible wires 28 increases from a first width $W_1$ for the flexible wires 28A positioned closer to a center line CL, to an intermediate second width $W_2$ for the flexible wires 28B that are positioned further from the center line, and then to a maximum width $W_3$ for the flexible wires 28C that are positioned furthest from the center line. In this embodiment, the particular width (W1, W2 or $W_3$) of each flexible wire is maintained along the length of each flexible wire 28 as the flexible wire extends from a catheter attachment portion 40 to a distal end 42 of the flexible wire 28. Each flexible wire 28 further comprises a transition portion 44 that extends distally from the catheter attachment portion 40 to the proximal end 46 of each flexible wire. The width of the transition portion 44 of each flexible wire generally has a width that is approximately equal to the width of the respective flexible wire 28. The length and curvature of the transition portions 44 vary depending on the position of the flexible wire 28. Generally, the transition portion 44 increases in length and curvature as the flexible wire 28 position is further from the center line CL. For example, those flexible wires 28A that are closer to the center line CL have a relatively short and straight transition portion 44A, those flexible wires 28B that are of an intermediate distance may be slightly longer and have a more pronounced curve, and the outer flexible wires 28C have a longer transition portion that curves substantially from the catheter attachment portion 40. The increase in width of the flexible wire and transition portion for those flexible wires that are positioned away from the center line CL increases the stability of the flexible wire as they bend away from the center line to form the brush-shaped spines that are on the periphery of the multi-electrode device 16.

FIG. 2B illustrates a side view of the flexible wire assembly 29 shown in FIG. 2A. FIG. 2B illustrates the thickness T of the flexible wires 28. In this embodiment, the thickness T is consistent for all of the flexible wires 28A to 28C and from the proximal end 46 to the distal end 42 of each flexible wire 28. However, the ratio of width to thickness in the flexible wires 28 increases from the narrowest flexible wire 28A to the widest flexible wire 28C. The width of the flexible spines may range from 0.005 inch to 0.020 inch. The thickness may range from 0.004" to 0.020". The ratio of width to thickness may range from 1:1 to 4:1, or higher depending on the application of the particular device. As illustrated the ratios of the spines may be 1.1:1 for flexible wires 28A, 1.5:1 for flexible wires 28B and 2:1 for flexible wires 28C. The resultant cross-sectional shape of the flexible wires with these ratios would range from a square to a rectangle. It should be noted that the embodiment described in FIG. 2A is merely illustrative, that the device may have more than six flexible wires and that the flexible wire assembly may have more, or less, than the three ratios depicted across the plurality of flexible wires. Those with ordinary skill will also appreciate that the ratio of width to thickness will depend on a number of factors, such as, the particular application of the device and the total number of spines included on the device. In the embodiment illustrated in FIGS. 2A and 2B, the increase in ratio of width to thickness of the flexible wires 28A, 28B, 28C as the position moves away from the center line CL provides an increase in stiffness to the flexible wire 28 to better stabilize those spines 18 that are further from the center of the deployed electrode device 16.

Referring now to FIGS. 3A and 3B, FIG. 3A is another embodiment of a flexible wire assembly 129 having a variable cross section. In this embodiment, the cross section tapers from a first width W11 at the proximal end 146 of flexible wire 128 to a width W12 at the distal end 142 of the flexible wire. The difference in width from W11 to W12 may be from 0.001" to 0.015". The increase in width for W11 provides a stiffer base portion to better support the spine and electrodes that cover the flexible wire assembly 129. The narrower width W12 at distal end 142 will increase the flexibility of the distal portion of the device and provide better electrode 20 contact with the tissue to be treated. The stiffness of the proximal end 146 and flexibility of the distal end 142 may be further increased by adjusting the thickness T of the flexible wires 128. FIG. 3B illustrates a side view of flexible wire 129 showing the thickness T. The flexible wire 128 may have a variable thickness of about 0.004" to 0.020". In one embodiment, the thickness of the flexible wires 128 tapers from a first thickness T1 to a second thickness T2. Similar to the difference in width discussed above, the difference in thickness T may be from about 0.001 to about 0.015". In another embodiment, the thickness does not vary along the length L where T1 is equal to T2. The embodiment of flexible wire assembly 129 illustrated in FIGS. 3A to 3B is similar in all other aspects to that of flexible wire assembly 29 illustrated in FIGS. 2A to 2B, above.

Figure 4:
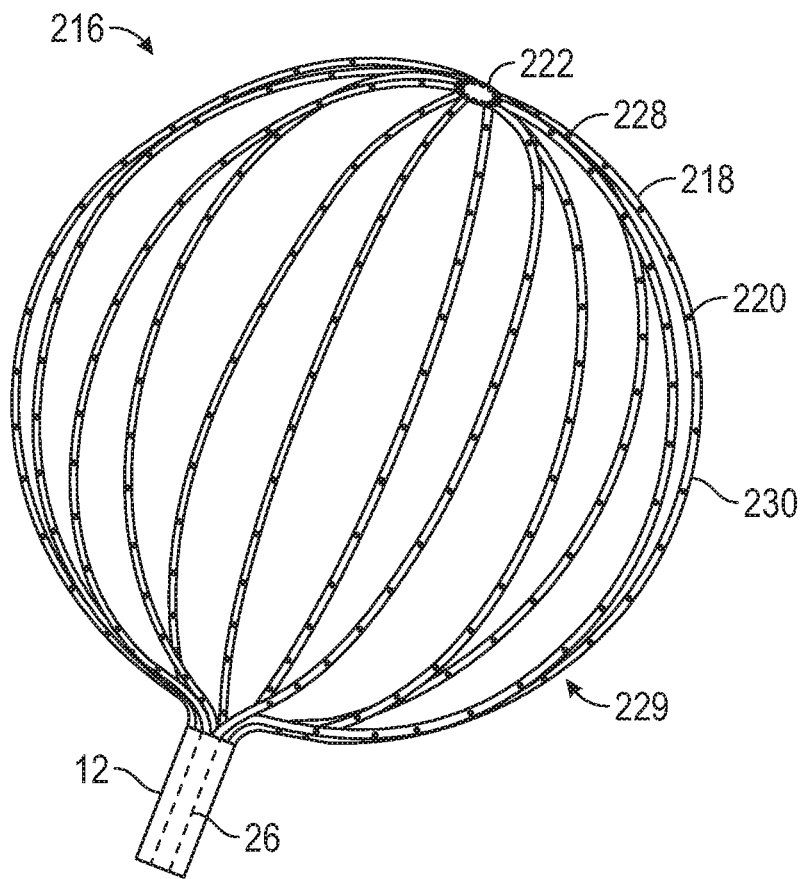
FIG. 4 is a detailed view of a basket-shaped multi-electrode assembly, according to another embodiment.

Referring now to FIG. 4, FIG. 4 illustrates a basket-shaped electrode assembly 216 suitable for using with a catheter such as catheter 12 shown in FIG. 1, above. Basket-shaped electrode assembly 216 is a multi-electrode assembly comprising a plurality of spines. In this embodiment, electrode assembly 216 is a basket-shaped electrode assembly 216 having a plurality of spines 218, each carrying multiple electrodes 220. To enable accurate mapping of electrical signals, it may be desirable to provide an array of electrodes with a relatively high density. As such, the number of spines 218 employed may vary from four to sixteen, or any other suitable number. The distal ends of spines 218 are separated from adjacent spines. Each spine 218 may include multiple electrodes 220, such as at least six and up to approximately sixteen electrodes per spine, or any other number of electrodes to suit a particular application. Similarly, the electrodes may be evenly distributed along the spine or may be skewed proximally, centrally or distally to facilitate analysis of the measured electrical signals. The distal ends of spines 218 are joined together at a distal hub 222. Distal hub 222 may take any form to suit a particular application. In one embodiment, distal hub 222 is a generally circular and flat structure to allow for more of the electrodes 220 to contact the tissue to be mapped or treated. In another embodiment, distal hub 222 is a columnar shape having spines joining the distal hub at a plurality of insertion points. Spines 218 may be evenly or unevenly distributed radially about distal hub 222. Spines 218 include a shape memory material, as described above, that facilitates assuming an expanded arrangement. When the basket-shaped electrode assembly 216 is deployed, it assumes an expanded configuration whereby the spines 218 bow outwards into contact or closer proximity with the walls of the chamber in which it has been deployed, such as the left atrium.

Each spine 218 may comprise a flexible wire 228 support with a non-conductive covering 230 on which one or more of the ring electrodes 220 are mounted. Each ring electrode 220 may be configured as monopolar or bipolar, as known in the art. In an embodiment, the flexible wires 228 may be formed from a shape memory material to facilitate the transition between expanded (deployed) and collapsed (delivery) configurations and the non-conductive coverings 230 may each comprise biocompatible plastic tubing, such as polyurethane or polyimide tubing. A plurality of flexible wires 28 may be joined to form a flexible wire assembly, discussed in more detail below in relation to FIGS. 5A and 5B.

As used herein, the term "basket-shaped" in describing the electrode assembly 216 is not limited to the depicted configuration, but can include other designs, such as spherical or egg-shaped designs, that include a plurality of expandable arms or spines connected, directly or indirectly, at their proximal and distal ends. In one aspect, different sized basket-shaped electrode assemblies may be employed depending on the patient's anatomy to provide a close fit to the area of the patient being investigated, such as the right or left atria. Other shapes for electrode assembly 216 are contemplated by the present invention.

As with the brush-shaped multi-electrode assembly illustrated and described in detailed, above, the underlying flexible wire assembly support for the basket-shaped multi-electrode will also benefit from improvements to the cross-section of the flexible wires that make up the flexible wire assembly. Further, the cross-sectional shape generally is square or rectangular. This shape also aids in the improved control and movement of the spines and electrodes.

Figure 5A:
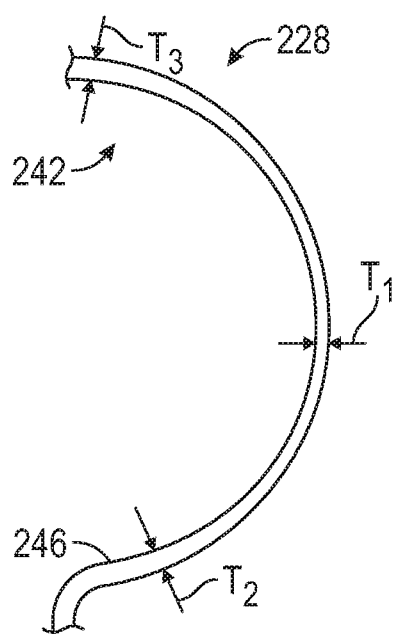
FIGS. 5A and 5B are schematic view of a portion of a basket-shaped flexible wire assembly, according to the embodiment of FIG. 4.
Figure 5B:
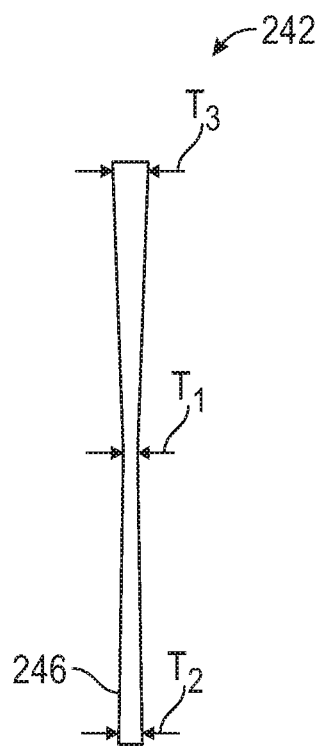

Referring now to FIGS. 5A and 5B, FIGS. 5A and 5B illustrates a flexible wire 228 of the flexible wire assembly 229 with a variable cross-section. In one embodiment, the thickness T of the flexible wire 228 varies from a first thickness T1 near the middle of the flexible wire 228 to a second thickness T2 adjacent the proximal end 246 of flexible wire 228. Flexible wire 228 may have a third thickness T3 located near the hub 222. FIG. 5B illustrates a straightened flexible wire 228 to better show the variable thicknesses. In this embodiment, the thickness of the flexible wire 228 tapers from thickness T3 at the distal end 242 towards the middle and also from thickness T2 at the proximal end 246 to the middle. In one embodiment thickness T2 is equal to thickness T3. The thickness of the flexible wire 228 ranges from 0.006" to 0.012". The difference in thickness from T1 to T2/T3 may be about 0.001 to about 0.006". In one embodiment, the width of the flexible wire remains essentially constant from the proximal end 246 to the distal end 242. In another embodiment, the width also varies similarly to the thickness. The dimensions of the width may be from 0.004" to 0.015".

One of ordinary skill in the art will appreciate that elements of each of the embodiments described above for FIGS. 2A to 5B may be combined with other elements from other embodiments and these combinations are within the scope of the invention. The following discussion of FIG. 6 also applies to each of the above described embodiments.

Figure 6:
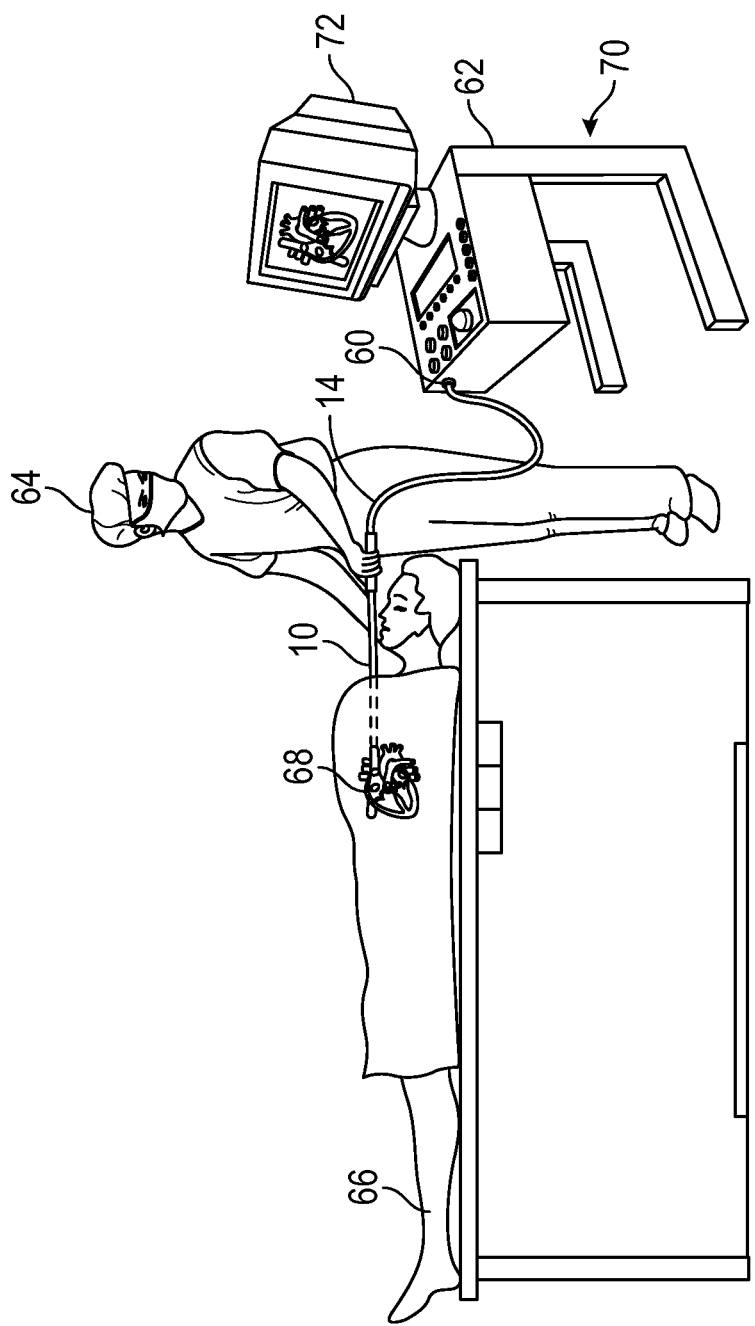
FIG. 6 is a schematic illustration of an invasive medical procedure using a multi-electrode assembly, according to one embodiment.

To help illustrate use of multi-electrode assembly 16, FIG. 6 is a schematic depiction of an invasive medical procedure, according to an embodiment of the present invention. Catheter 10, with electrode assembly 16 (See FIG. 1) at the distal end may have a connector 60 at the proximal end for coupling the wires from their respective electrodes 20 (See FIG. 1) to a console 62 for recording and analyzing the signals they detect. An electrophysiologist 64 may insert the catheter 10 into a patient 66 in order to acquire electropotential signals from the heart 68 of the patient. The professional uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals.

In a further aspect, the processing unit 70 may also receive signals from one or more location sensors 74 provided near a distal end of the catheter 10 adjacent the electrode assembly 16. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/005768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the electrode assembly 16. The coordinates of the distal sensor relative to the proximal sensor may be determined and, with other known information pertaining to the spines 18 of the electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated catheter body extending along a longitudinal axis, the elongated catheter body having a proximal end and a distal end;
a flexible wire assembly positioned at the distal end of the elongated catheter body formed from a shape memory material, the flexible wire assembly having a plurality of flexible wires, each flexible wire having a length between a proximal end and a distal end and wherein at least one of the flexible wires has a variable cross-section, the at least one flexible wire having a variable thickness along the entire length of the flexible wire where a middle portion of the flexible wire has a first thickness, a proximal portion of the flexible wire has a second thickness, the second thickness being greater than the first thickness, and a distal portion with a third thickness, the third thickness being greater than the first thickness, wherein along the length between the proximal end and the distal end, the thickness of the flexible wire gradually tapers from the distal portion to the middle portion; and wherein the thickness of the flexible wire gradually tapers from the proximal portion to the middle portion;
a plurality of spines formed from the plurality of flexible wires; and
a plurality of electrodes and cabling attached to each spine.

2. The catheter of claim 1, wherein the distal ends of the plurality of flexible wires are joined at a distal hub to form a basket shaped multi-electrode device.

3. The catheter of claim 1, wherein the second thickness is equal to the third thickness.

4. The catheter of claim 1, wherein the at least one flexible wire has a width that is constant from the proximal portion to the distal portion.

5. The catheter of claim 1 wherein the at least one flexible wire has a width that tapers from the proximal portion to the middle portion, and wherein the width tapers from the distal portion to the middle portion.

6. The catheter of claim 1, wherein the shape memory material comprises a nickel titanium alloy.

* * * * *